(12) United States Patent
Newton

(10) Patent No.: US 6,892,998 B2
(45) Date of Patent: May 17, 2005

(54) MEDICAL VALVE AND METHOD OF ASSEMBLING THE SAME

(75) Inventor: Brian L. Newton, Woonsocket, RI (US)

(73) Assignee: Nypro, Inc., Clinton, MA (US)

( * ) Notice: Subject to any disclaimer, the term of this patent is extended or adjusted under 35 U.S.C. 154(b) by 192 days.

(21) Appl. No.: 10/265,292

(22) Filed: Oct. 4, 2002

(65) Prior Publication Data

US 2003/0085372 A1 May 8, 2003

Related U.S. Application Data

(60) Provisional application No. 60/327,942, filed on Oct. 9, 2001.

(51) Int. Cl.$^7$ ................................................ A61M 5/00
(52) U.S. Cl. ..................... 251/149.1; 251/367; 251/904
(58) Field of Search ........................ 251/149.1, 149.6, 251/367, 904

(56) References Cited

U.S. PATENT DOCUMENTS

| 4,712,583 | A | 12/1987 | Pelmulder et al. ........... 137/852 |
| 5,025,829 | A | 6/1991 | Edwards et al. ............. 137/512 |
| 5,575,279 | A | 11/1996 | Beplate ................. 128/203.11 |
| 5,727,594 | A | 3/1998 | Choksi ........................ 137/859 |
| 5,746,414 | A | 5/1998 | Weldon et al. ........... 251/149.6 |
| 5,782,918 | A | 7/1998 | Klardie et al. ................ 623/16 |
| 5,992,461 | A | 11/1999 | Gilmore et al. ......... 137/625.65 |
| 6,036,171 | A | 3/2000 | Weinheimer et al. .... 251/149.1 |
| 6,079,432 | A | 6/2000 | Paradis .......................... 137/1 |
| 6,089,272 | A | 7/2000 | Brand et al. ................ 137/859 |
| 6,112,368 | A | 9/2000 | Luckett ......................... 16/59 |
| 6,156,025 | A | 12/2000 | Niedospial, Jr. et al. .... 604/408 |
| 6,168,137 | B1 | 1/2001 | Paradis .................... 251/149.6 |
| 6,245,048 | B1 | 6/2001 | Fangrow, Jr. et al. ....... 604/249 |
| 2002/0133124 | A1 | 9/2002 | Leinsing et al. ............ 604/256 |

FOREIGN PATENT DOCUMENTS

WO    WO 01/07102 A2    2/2001   ............ A61M/5/00

Primary Examiner—J. Casimer Jacyna
(74) Attorney, Agent, or Firm—Bromberg & Sunstein LLP

(57) ABSTRACT

A medical valve has a first housing portion and a second housing portion capable of mating with the first housing portion to form an interior. The medical valve also has a valving element within the interior. The first and second housing portions have mating longitudinal snap-fit structures for longitudinally mating the first housing portion to the second housing portion. The first and second housing portions also have mating rotational snap-fit structures for substantially preventing the first housing portion from rotating relative to the second housing portion when the longitudinal snap fit structures are mated.

28 Claims, 6 Drawing Sheets

MEDICAL VALVE AND METHOD OF ASSEMBLING THE SAME

PRIORITY

This patent application claims priority from provisional U.S. patent application No. 60/327,942, filed Oct. 9, 2001, entitled, "SNAP FIT MEDICAL VALVE," and naming Brian L. Newton as inventor, the disclosure of which is incorporated herein, in its entirety, by reference.

FIELD OF THE INVENTION

The invention generally relates medical valves and, more particularly, the invention relates to methods of assembling medical valves and structures facilitating their assembly.

BACKGROUND OF THE INVENTION

Medical valving devices typically valve fluids injected into and withdrawn from a patient. One principle function of a medical valve is to maintain a sealed port to the patient's vasculature. More specifically, a valve provides vascular access without requiring the patient's skin to be repeatedly pierced by a needle. Moreover, many types of medical valves are constructed to withstand a range of back-pressures produced by a patient's blood pressure, thus minimizing blood loss resulting from fluid injections or withdrawals.

The fluid control function of a valve typically is performed by a valve element contained within two or more connected housing portions. By way of example, one such medical valve is disclosed in U.S. Pat. No. 6,039,302 entitled, "SWABBABLE LUER-ACTIVATED VALVE," the disclosure of which is incorporated herein, in its entirety, by reference. The valve in that patent includes two housing portions that are ultrasonically welded together. The coupled housing portions together form an interior that contains a valve element for controlling fluid flow.

Ultrasonic welding the two housing portions, however, takes a relatively long time in the valve assembly process. Moreover, ultrasonic welding requires relatively complex and expensive capital equipment.

SUMMARY OF THE INVENTION

In accordance with one aspect of the invention, a medical valve has a first housing portion and a second housing portion capable of mating with the first housing portion to form an interior. The medical valve also has a valving element within the interior. The first and second housing portions have mating longitudinal snap-fit structures for longitudinally mating the first housing portion to the second housing portion. The first and second housing portions also have mating rotational snap-fit structures for substantially preventing the first housing portion from rotating relative to the second housing portion when the longitudinal snap fit structures are mated.

In some embodiments, the first and second housing portions are generally cylindrically shaped. Moreover, the longitudinal snap-fit structures may include a ridge protruding from the first housing portion and a corresponding groove formed in the second housing portion. The ridge and the groove may be formed about 360 degrees of the respective first and second housing portions.

The rotational snap-fit structures may include a first set of stops (on the first housing portion) having a first shape, and a second set of stops (on the second housing portion) having a second shape. The first shape corresponds with the second shape to substantially prevent rotational movement of the first housing portion relative to the second housing portion when the longitudinal snap-fit structures are mated. The first set of stops may include a set of protrusions and the second set of stops may include a set of dimples. The set of dimples may be shaped to cam the set of protrusions during assembly so that the set of protrusions are in registry with the plurality of dimples when the longitudinal snap-fit structures are mated. In some embodiments, there are more dimples than protrusions. In other embodiments, the first and second sets of stops includes flats. In addition, the longitudinal snap-fit structure on the first housing portion may be proximate to, but distinct from, the rotational snap-fit structure on the first housing portion.

In accordance with another aspect of the invention, a medical valve has a first housing portion having a first snap-fit structure, and a second housing portion having a second snap-fit structure that couples with the first snap fit structure to couple the first and second housing portions. The first snap-fit structure is shaped to cam the second snap-fit structure during assembly so that the first snap-fit structure is in registry with the second snap-fit structure when the first and second housing portions are coupled.

In accordance with another aspect of the invention, a method of assembling a medical valve provides a first housing portion having a first snap-fit structure, and a second housing portion having a second snap-fit structure. A valve element is inserted within the first housing portion, and the first snap-fit structure is mated with the second snap-fit structure to secure the valve element between the housing portions. During mating, the first snap-fit structure cams the second snap-fit structure to cause the first snap-fit structure to be in registry with the second snap-fit structure when assembled.

BRIEF DESCRIPTION OF THE DRAWINGS

The foregoing and advantages of the invention will be appreciated more fully from the following further description thereof with reference to the accompanying drawings wherein.

DESCRIPTION OF ILLUSTRATIVE EMBODIMENTS

In illustrative embodiments of the invention, a medical valve has a housing formed from inlet and outlet housing portions that are coupled via snap-fit structures. To that end, the housing portions have complimentary longitudinal and rotational snap-fit structures that facilitate their connection. The longitudinal snap-fit structures prevent the housing portions from being longitudinally separated, while the rotational snap-fit structures prevent the two housing portions from rotating relative to each other after assembly. Details of illustrative embodiments are discussed below.

Figure 1:
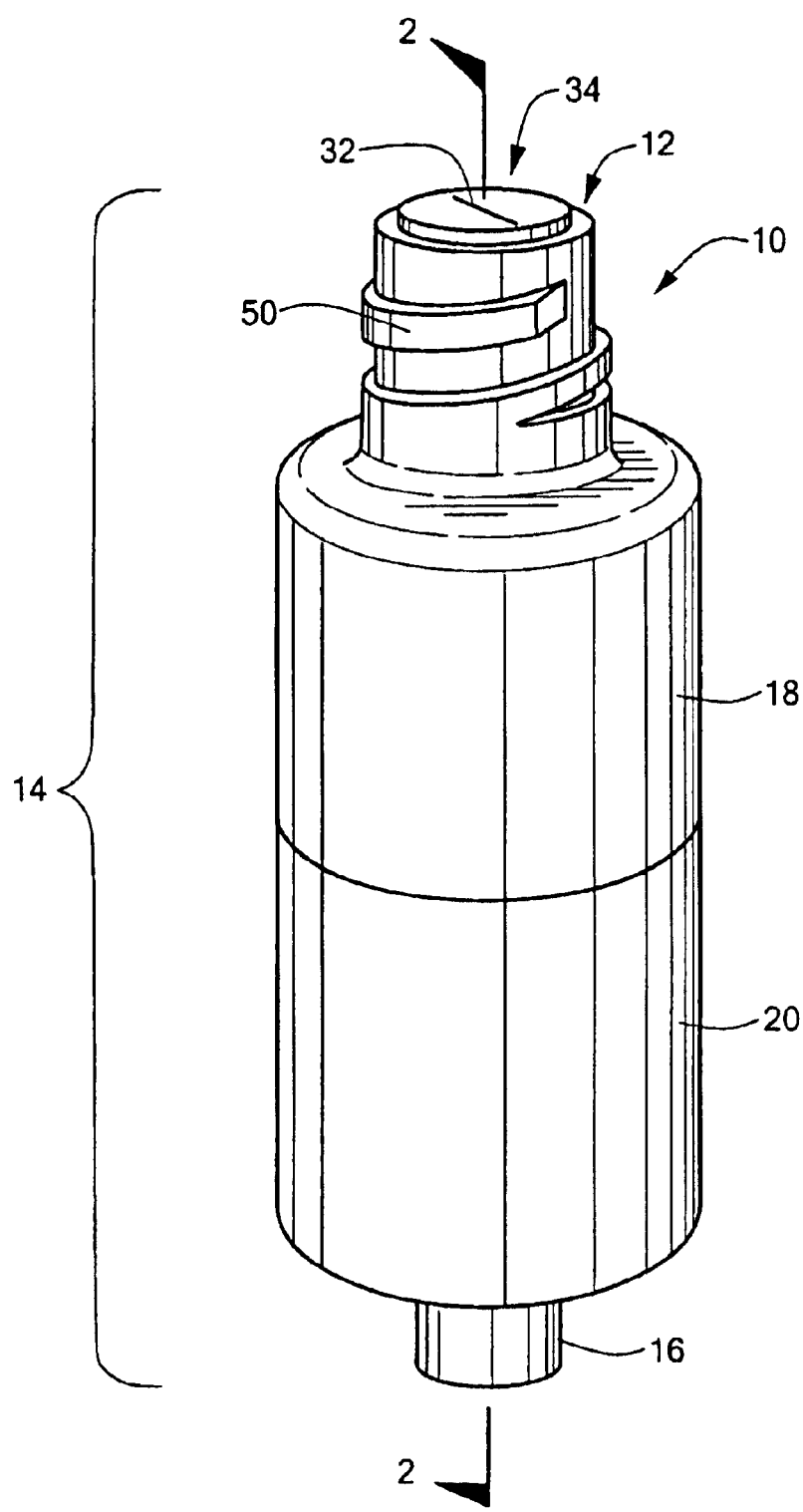
FIG. 1 schematically shows a medical valve that may be configured in accordance with illustrative embodiments of the invention.

FIG. 1 schematically shows a medical valve 10 having a housing 14 that may be configured an assembled in accordance with illustrative embodiments. More specifically, the valve 10 has a proximal port 12 (also referred to herein as "inlet 12") for receiving a nozzle (not shown), the housing 14 having a valving mechanism (shown in FIG. 2) that controls fluid flow through the valve 10, and a distal port 16 (also referred to herein as outlet 16) for directing fluid between the valve 10 and a patient. The fluid preferably is in liquid form, such as liquid medication, to pass through a centrally formed fluid channel (discussed in greater detail below). Although much of the discussion herein refers to the proximal port 12 as a fluid inlet, and the distal port 16 as a fluid outlet, the proximal and distal ports 12 and 16 also may be respectively used as outlet and inlet ports.

In illustrative embodiments, the valve 10 is similar to the swab valve disclosed in U.S. Pat. No. 6,039,302 entitled, "SWABBABLE LUERACTIVATED VALVE," the disclosure of which is incorporated herein, in its entirety, by reference. In addition, illustrative embodiments of the valve 10 also may be similar to co-pending and co-owned U.S. patent application Ser. No. 10/224,299, entitled, "MEDICAL VALVE WITH EXPANDABLE MEMBER," the disclosure of which is incorporated herein, in its entirety, by reference. Of course, various embodiments may relate to non-swab valves or other valve types and thus, such embodiments are not limited to swab valves. For example, embodiments of the invention may be applied to check valves.

Figure 2:
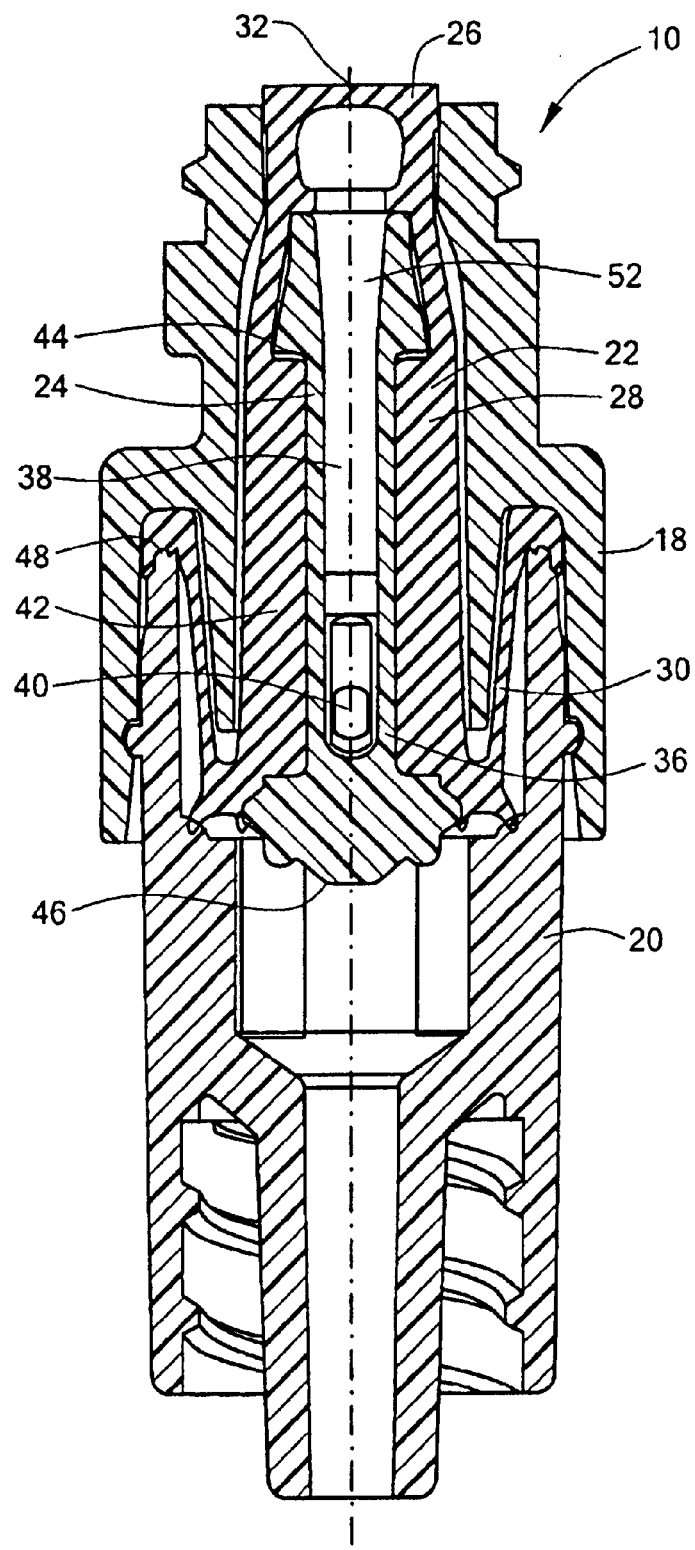
FIG. 2 schematically shows a cross-section of the medical valve shown in FIG. 1 along line 2—2.

FIG. 2 schematically shows a cross-sectional view of one embodiment of the medical valve 10 (shown in FIG. 1 along line 2—2) in a closed mode (i.e., preventing fluid flow). In summary, the valve 10 includes four snap-fit components. Specifically, the valve 10 includes an inlet housing 18 having the inlet 12, and an outlet housing 20 having the outlet 16. The two housing portions 18 and 20 together form the housing 14. The remaining two components cooperate to valve fluid through the housing 14. Specifically, the valve 10 also has a stretchable, resilient, and compressible member (referred to in various embodiments herein as "gland 22") secured between the inlet housing 18 and outlet housing 20, and a rigid, longitudinally movable plug 24 (also more generally referred to as a "plug member" due in part to its plugging function) secured within the valve 10 by the gland 22. Details of these four valve components and their cooperation are discussed below.

The first of these components to be discussed, gland 22, is considered to have three contiguous sections. In particular, those sections include a proximally located swabbable seal section 26 to provide a low pressure, proximally located seal, a tubular section 28 that cooperates with the plug 24 to control fluid flow, and an attachment section 30 to secure the gland 22 within the valve 10. Each of these sections of the gland 22 is discussed below.

More specifically, the seal section 26 has a normally closed aperture 32 to provide the above noted low pressure seal. Among other things, the aperture 32 may be, for example, a pierced hole or a slit formed to be normally closed when the valve 10 is in the closed mode. No radial force thus is required by the housing 14 to close the aperture 32. In fact, in some embodiments, the outer diameter of the seal section 26 is smaller than the inner diameter of the inlet 12. In alternative embodiments, however, the inner diameter of the inlet 12 is smaller than the outer diameter of the seal section 26 of the gland 22. Consequently, in such embodiments, the housing 14 squeezes the seal section 26, thereby forcing the aperture 32 closed. A nozzle or syringe thus may open the seal by deforming the seal section 26.

When the valve 10 is in the fully closed position, the seal section 26 is flush with, or extends slightly above, the exterior inlet face 34 of the housing 14. The seal section 26 and the exterior inlet face 34 thus present a swabbable surface. In other words, the seal section 26 and the exterior inlet face 34 may be easily wiped clean by any conventional means, such as with an alcohol swab. As mentioned in the above noted incorporated patent, valves having swabbable surfaces are known in the art as "swabbable valves." In other embodiments, however, the valve 10 is not a swabbable valve.

The second section of the gland 22, the tubular section 28, illustratively is both resilient and compressible. Accordingly, the tubular section 28 effectively acts as a spring to normally maintain the gland 22 in the closed mode. In addition, the tubular section 28 also cooperates with the plug 24 to provide a high pressure seal area 36. Specifically, the plug 24 has a plug flow channel 38 that makes up a portion of the overall fluid channel 52 through the valve 10 (discussed below). The plug flow channel 38 terminates at a transverse channel 40 that normally is occluded by the tubular section 28 (see FIG. 2). To that end, the outer diameter of the outlet end of the plug 24 is selected to match the inner diameter of a sealing portion of the gland 22 when in the closed mode. For example, the plug outlet end 46 may have a wider outer diameter than the inner diameter of the compressible, tubular section 28 of the gland 22. This high pressure seal area 36 thus is able to resist a large amount of back pressure from the outlet end of the valve 10. Moreover, since the valve 10 has this high pressure seal area 36, it is not necessary for the low pressure seal (i.e., the aperture 32 through the seal section 26) to resist large back pressures.

A portion of the tubular section 28 illustratively is preloaded by having a preload gland portion 42 that is slightly longer (when in its normal state) than the distance between a plug ledge 44 and the plug outlet end 46. For example, when in its normal state, the preload gland portion 42 may be about 0.005 inches longer than the noted plug distance. This preloading ensures that the preload gland portion 42 of the tubular section 28 is under compression in all modes/states. Consequently, the transverse channel 40 should be properly located relative to the tubular section 28 to maintain the high pressure seal area 36. Accordingly, preloading ensures that the high pressure seal area 36 maintains its sealing function. The valve 10 thus should resist opening in response to either a positive pressure or a negative pressure applied to the outlet 16.

In alternative embodiments (not shown in the drawings), the high pressure seal area 36 is configured differently. In such embodiment, the transverse channel 40 is not normally occluded by the tubular section 28 of the gland 22. Instead, the distal end of the plug 24 (also distal of the transverse channel) has an annular ledge that mates with the gland 22 to provide an annular seal distal of the transverse channel 40. Fluid draining from the transverse channel 40 thus is sealed by this mating structure.

The final one of the above listed gland sections, the attachment section 30, serves several important functions.

Primarily, it secures the gland 22 within the housing 14. To that end, the housing 14 includes a pair of opposing annular upstanding ridges 48 that normally are forced into the proximal and distal surfaces of the attachment section 30. In addition, the attachment section 30 rests on a relatively flat inner surface of the housing 14, thus providing a base from which the tubular section 28 can provide its spring (i.e., proximal biasing) functionality.

Figures 3A, 3B:
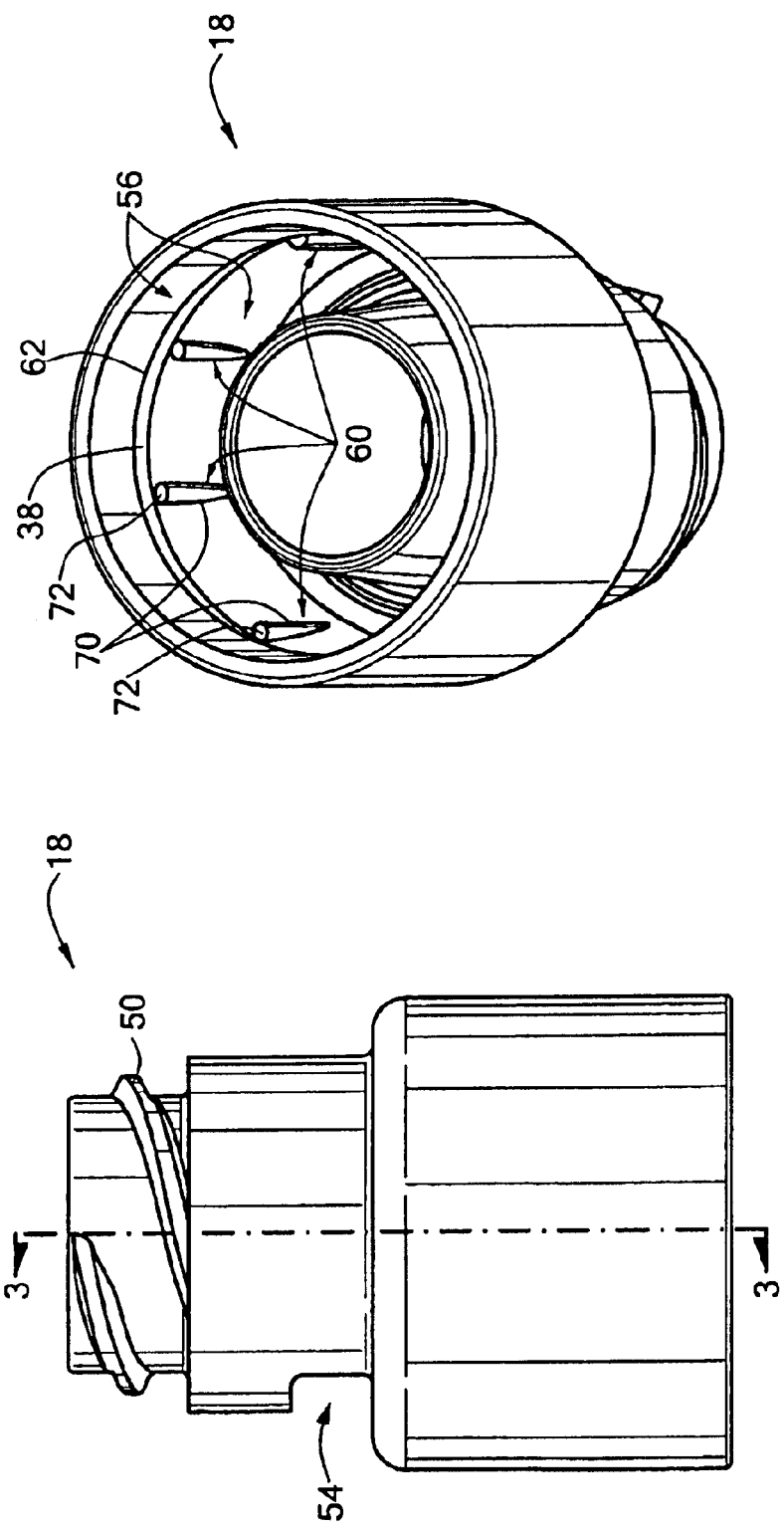
FIG. 3A schematically shows a side view of an embodiment of the inlet housing portion of the medical valve shown in FIG. 1.
FIG. 3B schematically shows a bottom view of the inlet housing portion shown in FIG. 3A.
Figures 3C, 4:
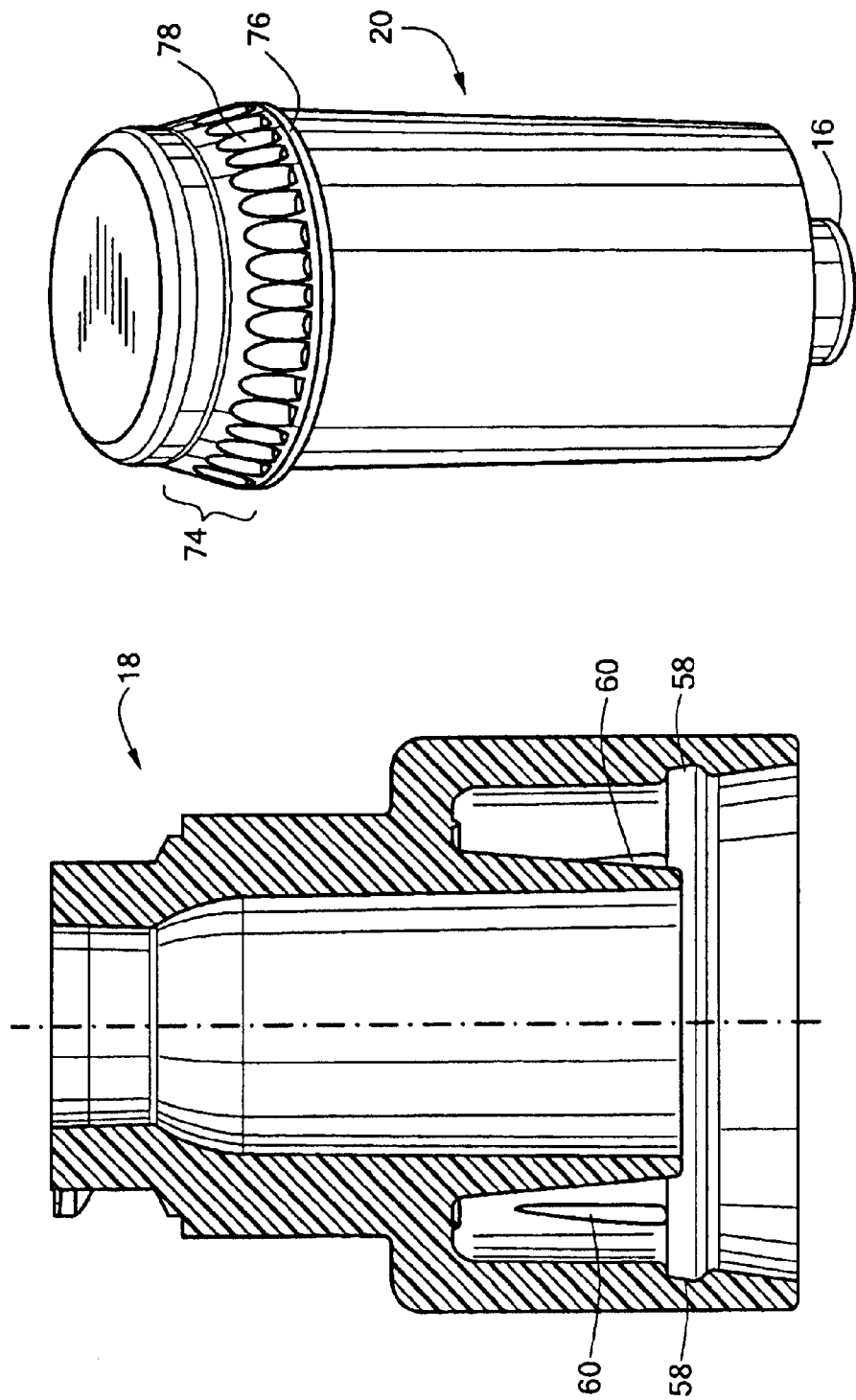
FIG. 3C schematically shows a cross-sectional view of the inlet housing shown in FIG. 3A along line 3—3.
FIG. 4 schematically shows an isometric view of an embodiment of the outlet housing portion of the medical valve shown in FIG. 1.

FIGS. 3A–3C show three different views of one embodiment of the inlet housing 18. Specifically, FIG. 3A schematically shows a side view of an embodiment of the inlet housing 18 of the medical valve 10 shown in FIG. 1. To see the interior of the inlet housing 18, FIG. 3B schematically shows a bottom view of the inlet housing 18 shown in FIG. 3A. Finally, FIG. 3C schematically shows a cross-sectional view of the inlet housing 18 shown in FIG. 3A along line 3—3.

As shown in each of these figures, the inlet housing 18 has a generally cylindrical shape. More particularly, although the inlet housing 18 has threads 50 and an indent 54, its overall shape is generally cylindrical. Because of this shape (and the generally cylindrical shape of the outlet housing 20, discussed below), the inlet housing 18 will rotate relative to the outlet housing 20 if no structure is included to prevent such rotation. In other words, the portions of the inlet and outlet housings 18 and 20 that mate to snap-fit together are generally cylindrical and thus, require some structure to ensure that they cannot rotate relative to each other. A housing thus is considered to be generally cylindrical at least when the inlet and outlet housings 18 and 20 require structure to prevent their relative rotation.

To these ends, FIGS. 3B and 3C show an inlet housing snap-fit structure 56, which includes a longitudinal snap-fit structure (hereinafter, "inlet longitudinal structure 58") to longitudinally secure the inlet housing 18 to the outlet housing 20, and a rotational snap-fit structure (hereinafter, "inlet rotational structure 60") to prevent the inlet and outlet housings 18 and 20 from rotating relative to one another. As discussed below, the geometry and size of the inlet housing snap-fit structure 56 are selected relative to the snap-fit structures of the outlet housing 20 (discussed below with reference to FIG. 4) to securely couple the two housing portions.

As noted above, the inlet longitudinal structure 58 of the inlet housing 18 illustratively includes a structure that mates (i.e., couples) with a corresponding longitudinal snap-fit structure on the outlet housing 20. For example, as shown in FIGS. 3B and 3C, such structure may be a groove (also identified by reference number "58") formed along the entire inner periphery of the inlet housing 18. The groove 58 can have a leading edge 62 and a trailing edge to lock a mating ridge of the outlet housing 20, or merely a leading edge to prevent the two housing portions from uncoupling. This connection may be referred to in the art as a "mechanical fit" or an "interference fit." Details of this cooperation are discussed below with reference to FIG. 6.

The inlet rotational structure 60 of the inlet housing 18 illustratively includes a plurality of stops that are formed to mate with corresponding stops of the outlet housing 20. When mated, under expected conditions, the inlet and outlet housings 18 and 20 should not rotate relative to each other. The stops shown in the embodiment of FIGS. 3A–3C are a plurality of protrusions (also identified by reference number "60") formed about the inner periphery of the inlet housing 18. Each protrusion 60 extends in a longitudinal direction and is identical. Moreover, each protrusion 60 includes a uniform diameter shaft 70 that terminates at a rounded end 72 adjacent to the groove 58. More broadly, instead of a rounded end 72, each protrusion 60 may be considered to have a tapered end 72 (i.e., a smaller diameter than that of the shaft 70) that facilitates coupling with the stops on the outlet housing 20. Details of coupling are discussed below.

The protrusions 60 shown in FIGS. 3B and 3C terminate a very short distance from the leading edge 62 of the groove 58. This short distance illustratively is based upon the geometry of the corresponding structures in the outlet housing 20. Although they cooperate and are adjacently positioned, the shown inlet rotational structure 60 and inlet longitudinal structure 58 illustratively are separate components of the inlet housing 18. Stated differently, in such embodiments, although they may cooperate to some extent, each of the two structures can provide their respective functions if more distance separated them on the inlet housing 18. In other embodiments, however, the protrusions 60 are more intimately associated with the groove 58 and thus, both structures 58 and 60 are considered to be the same structure.

The inner diameter of the inlet housing 18 illustratively is slightly tapered (e.g., approximately 2–5 degrees) from the open end (that couples with the outlet housing 20) to the proximal port 12. As discussed below, this taper facilitates coupling between the inlet and outlet housings 18 and 20. The protrusions 60, however, illustratively are not configured to follow this taper. Instead, the proximal ends of the protrusions 60 merge into the inner periphery of the inlet housing 18.

FIG. 4 schematically shows an isometric view of an embodiment of the outlet housing 20 of the medical valve 10 shown in FIG. 1. In a manner similar to the inlet housing 18, the outlet housing 20 has a generally cylindrical shape. In addition, the outlet housing 20 also has an outlet housing snap-fit structure 74, which includes a longitudinal snap-fit structure and a rotational snap-fit structure. The longitudinal snap-fit structure (hereinafter, "outlet longitudinal structure 76") has a geometry that permits it to securely mate with the inlet longitudinal structure 58. In the embodiment shown in FIGS. 2–4, the outlet longitudinal structure 76 includes an upstanding ridge (also identified by reference number "76") extending around the outer periphery of the outlet housing 20.

The rotational snap-fit structure (hereinafter, "outlet rotational structure 78") illustratively includes a plurality of stops that are formed to mate with corresponding stops of the inlet housing 18. The stops on the outlet housing 20 thus are a plurality of dimples (also identified by reference number "78") formed about the outer periphery of outlet housing 20. The dimples 78 are sized to have a complimentary geometry and size to that of the protrusions 60. Accordingly, when coupled, each protrusion 60 on the inlet housing 18 securely fits within one of the dimples 78. To that end, each dimple 78 illustratively is identically shaped and sized to have a substantially oval shape that terminates in an abrupt flat surface formed by the ridge 76. The oval portion of each dimple 78 is near the open end of the outlet housing 20. As discussed in greater detail below, the oval dimple shape acts as a cam to the protrusions 60, thus enabling the two housing portions to appropriately align when assembled. Other dimple shapes may be used, however, to provide the camming function.

In illustrative embodiments, there are more dimples 78 than protrusions 60. In other embodiments, however, the valve 10 may have equal numbers of dimples 78 and protrusions 60, or more protrusions 60 than dimples 78. In the latter case, the dimple shape should accommodate more than one protrusion 60. Among other things, the total number of protrusions 60 may be based upon the rotational resistance provided by each coupled protrusion 60 and dimple 78. The embodiment shown, for example, has eight protrusions 60. A single protrusion 60 may be used if the rotational resistance provided by it and a corresponding dimple 78 is sufficient under expected rotational forces. Such rotational forces may include expected handling by medical personnel and rotational forces applied when a nozzle or syringe is inserted into the proximal port 12 (e.g., by screwing over the threads 50 at the proximal end of the inlet housing 18)

The dimples 78 shown in FIG. 4 terminate at the leading edge of the ridge 76. This termination illustratively is based upon the geometry of the corresponding structures in the inlet housing 18. The outlet rotational structure 78 thus is considered to be connected to, but separate from, the outlet longitudinal structure 76. For example, this embodiment should provide the same functionality if the dimples 78 were spaced farther from the ridge 76 (i.e., where each dimple 78 is not considered to form a small portion of the ridge 76). In such case, however, the leading edge would not be interrupted by the many dimples 78. In other embodiments, the two structures 76 and 78 illustratively are more intimately associated and thus, are considered to be the same structure.

In a manner that corresponds to the inlet housing 18, the outer diameter of the outlet housing 20 illustratively is slightly tapered (e.g., approximately 2–5 degrees) at least from the ridge 76 to the open end. As noted below, this taper facilitates coupling between the inlet and outlet housings 18 and 20. The dimples 78, however, illustratively are not configured to follow this taper. Instead, the dimples 78 get deeper as they extend distally.

In alternative embodiments, rather than have dimples 78 and corresponding protrusions 60, the stops can be complimentary protrusions extending from the respective housings. Other types of stops also may be used. One such additional type of stops is discussed below with regard to FIG. 7.

Figure 5:
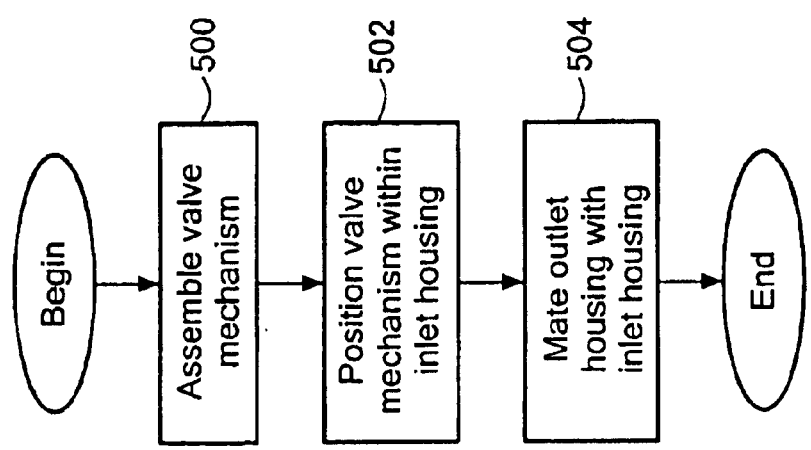
FIG. 5 shows a process of assembling the valve shown in FIG. 1 in accordance with illustrative embodiments of the invention.

FIG. 5 shows an illustrative process of assembling the valve 10. The process begins at step 500, in which the valve mechanism is assembled. To accomplish this, the plug member 24 is inserted into the gland 22 in the manner shown in FIG. 2.

The process then continues to step 502, in which the valve mechanism is positioned within the inlet housing 18. The outlet housing 20 then is mated (i.e., coupled) to the inlet housing 18 via their corresponding snap-fit structures (step 504). To that end, the inlet housing snap-fit structure 56 mates with the outlet housing snap-fit structure 74, thus causing the two housing portions to be in registry. In the embodiment shown in FIGS. 2–4, the ridge 76 of the (male) outlet housing 20 is urged into (i.e., urged proximal of) the groove 58 of the (female) inlet housing 18. Structure within the housing 14 prevents further longitudinal movement of the housing portion.

Figure 6:
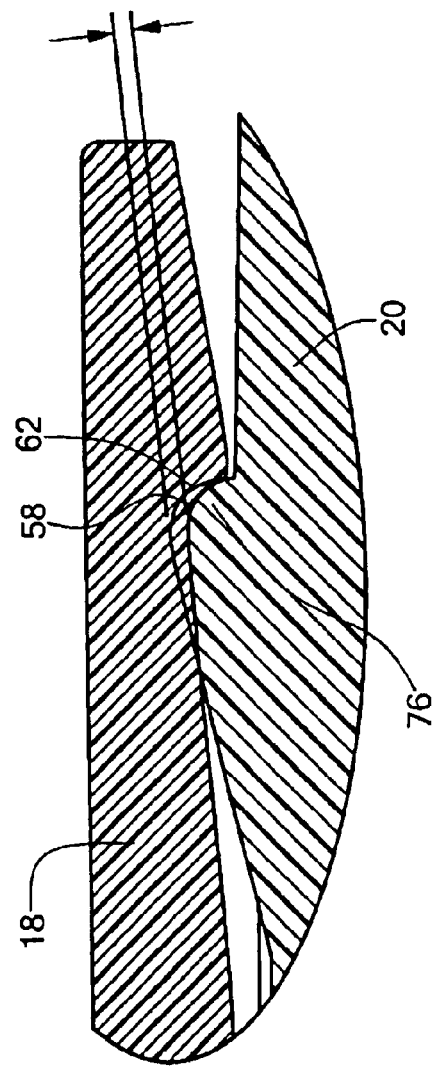
FIG. 6 schematically shows an enlarged view of the snap-fit between the inlet and outlet housing portions of various embodiments of the invention.

FIG. 6 schematically shows the interference fit between the two structures. In particular, the leading edge 62 of the groove 58 abuts the trailing edge of the ridge 76. FIG. 6 shows that the leading edge of the ridge 76 rides up the tapered inner surface of the inlet housing 18 as the two parts are being mated. This causes the inlet housing 18 to gradually stretch radially until the two parts mate. When mated, the inlet housing 18 contracts to its substantially normal diameter, thus locking the ridge 76 within the groove 58.

At the same time, the rotational snap-fit structures mate to prevent relative rotation of the two housing portions. Specifically, in the embodiments shown in FIGS. 2–4, when executing step 504, the protrusions 60 are urged toward the dimples 78. It is expected that, in many instances, the protrusions 60 will not be urged directly in a straight line into their corresponding dimples 78. If directly urged, however, the protrusions 60 should firmly seat in their respective dimples 78 because of their corresponding geometries. Instead, however, it is expected that during the assembly process (i.e., during step 504), the protrusions 60 will be off-center relative to the dimples 78. In such case, as the housings 18 and 20 are urged toward one another, the rounded end of the protrusions 60 cam against the oval walls of the dimples 78, thus forcing at least one of the two housing portions to rotate a small distance. This camming permits the protrusions 60 to seat in registry in their dimples 78. In other words, the camming causes the two housings 18 and 20 to align properly without external assistance (for alignment).

When coupled, the mated longitudinal snap-fit structures prevent the two housing portions from being separated under expected conditions. In a corresponding manner, under expected conditions, the mated rotational snap-fit structures prevent the two housings 18 and 20 from rotating relative to each other. As noted above, in various embodiments, the two snap-fit structures on each housing 18 or 20 are separate and thus, should be able to perform their designated functions if the other were not on the same valve 10. Such a valve 10 (i.e., having only one of the two noted snap-fit structures), however, would not be effective since it would lack the function of the absent snap-fit structure.

Accordingly, use of embodiments of the invention should permit high speed assembly because no welding is necessary. The two housing portions merely are forced in registry with one another.

Figure 7:
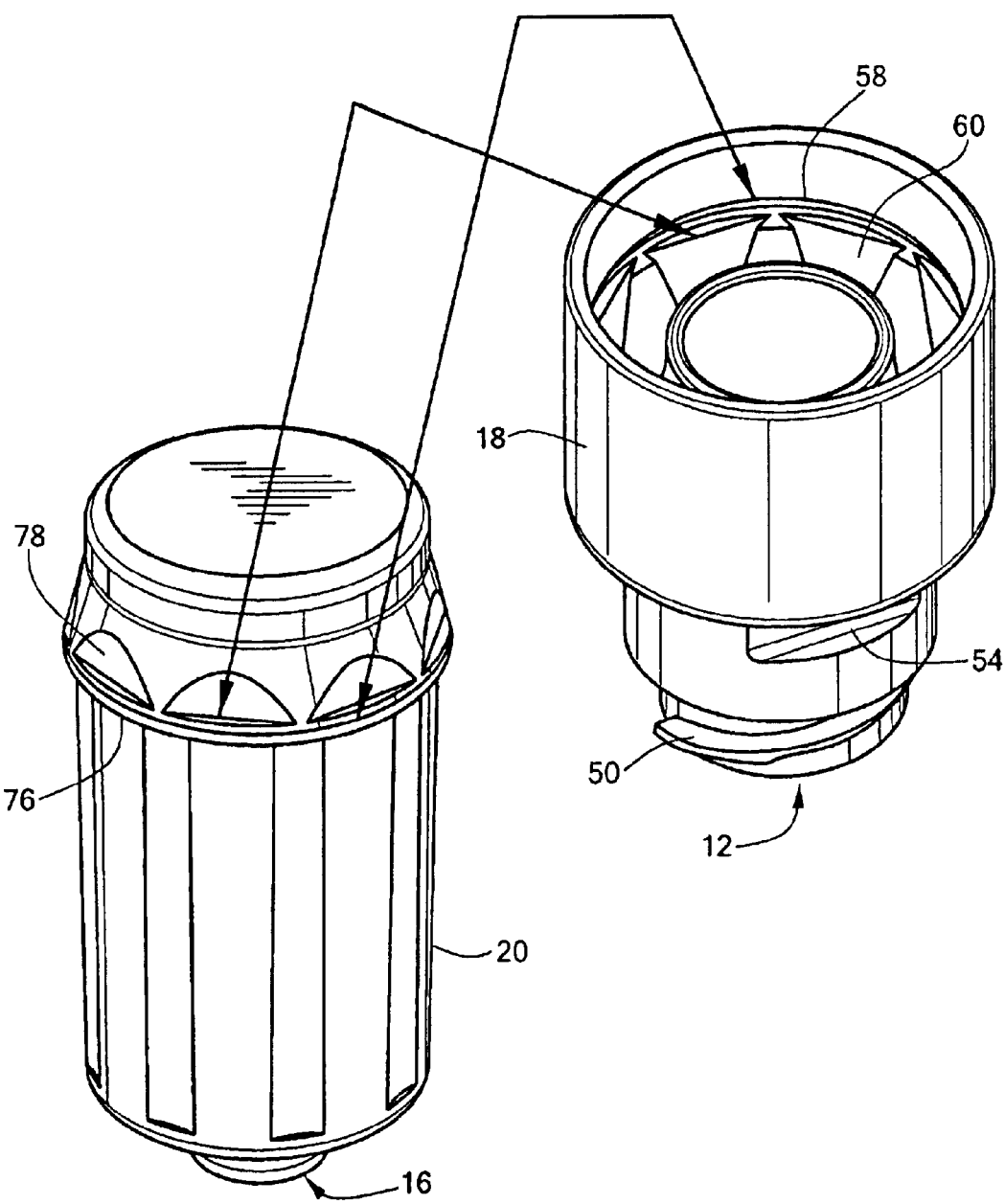
FIG. 7 schematically shows an alternate inlet and outlet housing that may be used for the valve shown in FIG. 1.

FIG. 7 schematically shows an alternative embodiment of the invention, in which the rotational snap-fit structures on both the inlet and outlet housings 18 and 20 are substantially the same. Specifically, the stops on the inlet and outlet housings 18 and 20 are flats having faces that, when assembled, are flush against each other. When the flats contact in that manner, the housing portions cannot rotate relative to each other (under expected conditions).

In yet other embodiments, the longitudinal snap-fit structures do not span the entire peripheries of their respective housing portions. Rather, selected portions of the housing peripheries have mating longitudinal snap-fit structures.

Although various exemplary embodiments of the invention are disclosed below, it should be apparent to those skilled in the art that various changes and modifications can be made that will achieve some of the advantages of the invention without departing from the true scope of the invention.

What is claimed is:

1. A medical valve comprising;

a first housing portion;

a second housing portion capable of mating with the first housing portion to form an interior; and a valving element within the interior, the first and second housing portions having mating longitudinal snap-fit structures for longitudinally coupling the first housing portion to the second housing portion, the first and second housing portions also having mating rotational snap-fit structures for substantially preventing the first housing portion from rotating relative to the second housing portion when the longitudinal snap fit structures are coupled, the rotational snap-fit structures being spaced from the longitudinal snap fit structures, wherein the rotational snap-fit structures comprise:

a first set of stops on the first housing portion, the first set of stops having a first shape;

a second set of stops on the second housing portion, the second set of stops having a second shape, the first shape corresponding with the second shape to substantially prevent rotational movement of the first housing portion relative to the second housing portion when the longitudinal snap-fit structures are coupled, wherein the first and second sets of stops includes flats for preventing rotational movement.

2. The medical valve as defined by claim 1 wherein the first and second housing portions are generally cylindrically shaped.

3. The medical valve as defined by claim 1 wherein the longitudinal snap-fit structures include a ridge protruding from the first housing portion and a corresponding groove formed in the second housing portion.

4. The medical valve as defined by claim 3 wherein the ridge and groove are formed about 360 degrees of the respective first and second housing portions.

5. The medical valve as defined by claim 1 wherein the first set of stops includes a set of protrusions and the second set of stops includes a set of dimples.

6. The medical valve as defined by claim 5 wherein the set of dimples are shaped to cam the set of protrusions during assembly so that the set of protrusions are in registry with the plurality of dimples when the longitudinal snap-fit structures are coupled.

7. The medical valve as defined by claim 6 wherein there are more dimples than protrusions.

8. The medical valve as defined by claim 1 wherein the longitudinal snap-fit structures on the first housing portion are proximate to, but distinct from, the rotational snap-fit structures on the first housing portion.

9. A medical valve comprising:

a first housing portion having a first snap-fit structure; and a second housing portion having a second snap-fit structure that couples with the first snap fit structure to couple the first and second housing portions, the first snap-fit structure being shaped to cam the second snap-fit structure during assembly so that the first snap-fit structure is in registry with the second snap-fit structure when the first and second housing portions are coupled, wherein the first set of stops includes a set of protrusions and the second set of stops includes a set of dimples, the valve having more dimples than protrusions.

10. The medical valve as defined by claim 9 wherein the first and second snap-fit structure has mating longitudinal snap-fit structures for longitudinally mating the first housing portion to the second portion, the first and second snap-fit structures also having mating rotational snap-fit structures for substantially preventing the first housing portion from rotating relative to the second housing portion when the longitudinal snap fit structures are mated.

11. The medical valve as defined by claim 9 wherein the first snap-fit structure includes a ridge protruding from the first housing portion, the second snap-fit structure having a corresponding groove formed in the second housing portion.

12. The medical valve as defined by claim 9 wherein the first snap-fit structure includes a first set of stops having a first shape, the second snap-fit structure including a second set of stops having a second shape, the first shape corresponding with the second shape to substantially prevent rotational movement of the first housing portion relative to the second housing portion when the housing portions are coupled.

13. A medical valve comprising:

a first housing portion; and a second housing portion; and means for snap-fit coupling the first housing portion to the second housing portion, the snap-fit coupling means including substantially radially facing flat snap-fit means for preventing the first housing portion from rotating relative to the second housing portion when the first and second housing portions are coupled.

14. The medical valve as defined by claim 13 wherein the snap-fit coupling means includes first snap-fit coupling means on the first housing portion and second snap-fit coupling means on the second housing portion, the first snap-fit coupling means including means for camming at least one of the first housing portion and second housing portion during assembly to enable the first and second snap-fit coupling means to be in registry when the housing portions are coupled.

15. The medical valve as defined by claim 13 wherein the snap-fit coupling means includes snap-fit means for longitudinally mating the first housing portion to the second housing portion.

16. The medical valve as defined by claim 1 wherein the first set of stops has respective first faces, the second set of stops having respective second faces, the first and second faces facing substantially in a radial direction, the first and second faces being substantially flat.

17. A medical valve comprising:

a first housing portion;

a second housing portion capable of mating with the first housing portion to form an interior; and a valving element within the interior, the first and second housing portions having mating longitudinal snap-fit structures for longitudinally coupling the first housing portion to the second housing portion, the longitudinally snap-fit structures including a ridge protruding from the first housing portion and a corresponding groove formed in the second housing portion, the first and second housing portions also having mating rotational snap-fit structures for substantially preventing the first housing portion from rotating relative to the second housing portion when the longitudinal snap fit structures are coupled.

18. The medical valve as defined by claim 17 wherein the ridge and groove are formed about 360 degrees of the respective first and second housing portions.

19. The medical valve as defined by claim 17 wherein the rotational snap-fit structures comprise a first set of stops on the first housing portion and a second set of stops on the second housing portion, the first set of stops including a set of protrusions and the second set of stops includes a set of dimples.

20. The medical valve as defined by claim 19 wherein the set of dimples are shaped to cam the set of protrusions during assembly so that the set of protrusions are in registry with the plurality of dimples when the longitudinal snap-fit structures are coupled.

21. The medical valve as defined by claim 17 wherein the rotational snap-fit structures comprise a first set of stops on the first housing portion and a second set of stops on the second housing portion, the first set of stops having a first number of stops, the second set of stops having a second number, the first number being greater than the second number.

22. The medical valve as defined by claim 17 wherein the longitudinal snap-fit structure on the first housing portion is proximate to, but distinct from, the rotational snap-fit structure on the first housing portion.

23. A medical valve comprising:

a first housing portion;

a second housing portion capable of mating with the first housing portion to form an interior; and a valving element within the interior, the first and second housing portions having mating longitudinal snap-fit structures for longitudinally coupling the first housing portion to the second housing portion, the first and second housing portions also having mating rotational snap-fit structures for substantially preventing the first housing portion from rotating relative to the second housing portion when the longitudinal snap fit structures are coupled, the rotational snap-fit structures being spaced from the longitudinal snap fit structures.

24. The medical valve as defined by claim 23 wherein the ridge and groove are formed about 360 degrees of the respective first and second housing portions.

25. The medical valve as defined by claim 23 wherein the rotational snap-fit structures comprise a first set of stops on the first housing portion and a second set of stops on the second housing portion, the first set of stops including a set of protrusions and the second set of stops includes a set of dimples.

26. The medical valve as defined by claim 25 wherein the set of dimples are shaped to cam the set of protrusions during assembly so that the set of protrusions are in registry with the plurality of dimples when the longitudinal snap-fit structures are coupled.

27. The medical valve as defined by claim 23 wherein the rotational snap-fit structures comprise a first set of stops on the first housing portion and a second set of stops on the second housing portion, the first set of stops having a first number of stops, the second set of stops having a second number, the first number being greater than the second number.

28. The medical valve as defined by claim 23 wherein the longitudinal snap-fit structures on the first housing portion are proximate to, but distinct from, the rotational snap-fit structures on the first housing portion.

* * * * *